United States Patent [19]

Fischer et al.

[11] Patent Number: 5,043,280

[45] Date of Patent: Aug. 27, 1991

[54] METHOD AND APPARATUS FOR THE MANUFACTURE OF A PRODUCT HAVING A SUBSTANCE EMBEDDED IN A CARRIER

[75] Inventors: Wilfried Fischer, Burscheid; Bernd W. Müller, Flintbek, both of Fed. Rep. of Germany

[73] Assignee: Schwarz Pharma AG, Monheim/Rhld, Fed. Rep. of Germany

[21] Appl. No.: 287,918

[22] Filed: Dec. 21, 1988

[30] Foreign Application Priority Data

Dec. 28, 1987 [DE] Fed. Rep. of Germany ....... 3744329

[51] Int. Cl.$^5$ .................... C12N 7/00; C12N 11/02; C12M 1/00; A61K 9/14
[52] U.S. Cl. ................... 435/235.1; 210/634; 264/13; 422/255; 422/280; 422/281; 424/409; 424/489; 435/174; 435/177; 435/180; 435/182; 435/287; 435/288; 435/311; 435/313
[58] Field of Search .............. 435/174, 177, 178, 180, 435/182, 235, 288, 311, 313, 287; 424/409, 489; 210/634; 264/13; 422/255, 280, 281

[56] References Cited

U.S. PATENT DOCUMENTS

| 3,773,919 | 11/1974 | Boswell, Jr. et al. | 424/19 |
| 4,489,055 | 12/1984 | Couvreur et al. | 424/7.1 |
| 4,820,537 | 4/1989 | Katz | 426/481 |
| 4,824,570 | 4/1989 | Bethuel et al. | 210/511 |
| 4,828,702 | 5/1989 | Coenen et al. | 210/634 |

FOREIGN PATENT DOCUMENTS 0052510  5/1982  European Pat. Off. .

OTHER PUBLICATIONS

Benitz et al., Journal of Pharmaceutical Sciences, vol. 73, No. 12, 1984, pp. 1721–1723.
T. R. Tice et al. "Preparation of Injectable Controlled-Release Microcapsules . . . Evaporation Process", Journal of Controlled Release 2 (1985) 343–352.
L. M. Sanders et al. "Controlled Delivery of an LHRH Analogue . . . Microspheres", Journal of Controlled Release 2 (1985) 187–195.
Franz P. Schmitz, "Chromatography with Sub- and Supercritical Eluents—Influence of the Separation Conditions . . . Number and Resolution", Journal of Chromatography, 356 (1986) 261–269.
L. M. Sanders et al. "Prolonged Controlled-Release of Nafarelin, A Luteinizing Hormone-Releasing Hormone (List continued on next page.)

*Primary Examiner*—David M. Naff
*Attorney, Agent, or Firm*—Marshall, O'Toole, Gerstein, Murray & Bicknell

[57] ABSTRACT

A sterile product containing a substance embedded in a carrier is produced by use of a supercritical gas. In one embodiment, a mixture is formed of a substance, carrier and supercritical gas such as nitrous oxide or carbon dioxide, and the supercritical gas is separated from the substance and carrier to obtain the product. In another embodiment, the supercritical gas contains the substance, and is mixed with an atomized organic solvent containing the carrier to form a mixture. The supercritical gas extracts the solvent, and is separated from the substance and carrier to produce the product. Alternatively, the carrier can be in the supercritical gas and the substance in the solvent, or both the substance and carrier can be in the solvent. Atomization and formation of the mixture can be carried out by feeding the supercritical gas and solvent through a nozzle into a spray tower or column. The supercritical gas containing the solvent is separated to obtain the product in the form of a dry powder containing spheres of the carrier having the substance embedded therein. The carrier can be polymers, lipids, lecithins or waxes, and the substance can be medicines, toxins, viruses, diagnostic materials, herbicides, insecticides or pesticides. An apparatus for carrying out the method contains a spray tower and other means for performing the method steps.

19 Claims, 5 Drawing Sheets

OTHER PUBLICATIONS

Analog, . . . Weight of Polymer", Journal of Pharmaceutical Sciences, vol. 75, No. 4, Apr. 1986—356–360.

J. P. Benoit et al. "A Physicochemical Study of the Morphology of Progesterone-Loaded Poly (D.L-lactide) Microspheres", International Journal of Pharmaceutics, 29 (1986) 95–102.

G. Birrenbach et al. "Polymerized Micelles and Their Use as Adjuvants in Immunology", vol. 65, No. 12, Dec. 1976, 1763–1766.

A. D. Schwope et al. "Lactic/Glycolic Acid Polymers as Narcotic Antagonist Delivery Systems", Life Sciences, vol. 17, pp. 1877–1886.

D. L. Wise et al. "Sustained Release of an Antimalarial Drug Using a Copolymer of Glycolic/Lactic Acid", Life Sciences, vol. 19, pp. 867–874, 1976.

METHOD AND APPARATUS FOR THE MANUFACTURE OF A PRODUCT HAVING A SUBSTANCE EMBEDDED IN A CARRIER

This invention pertains to a method and apparatus for the manufacture of a product comprising an active substance and a carrier.

BACKGROUND OF THE INVENTION

The effective long-term use of medicines is limited, among other reasons, by frequent administration of the medicine and a resulting problem of compliance by the patient. The use of medicaments in dosages taken one or several times daily for months or years, in the long run, leads to an uncertain intake and, consequently, to variable effectiveness.

A medicine which is only absorbed to a small extent when administered orally or through the skin or mucous membrane must be injected. The daily injection of a medical product over a long term is unpleasant for the patient since it is often painful.

Further, there is a large number of medical products which decompose in the injected area and are metabolized with a resulting pharmacokinetic profile which is unsatisfactory.

Medical compositions have been disclosed in the literature consisting of a medically active substance incorporated into a polymer matrix from which the medicine is gradually released. These medicine-embedded compositions can either be injectable or implantable-type medicines. Thus, for example, the DE-OS 3 428 372 describes the impregnating or embedding of pharmaceutically active peptides in poly D(−)-3-hydroxy butyric acid, and the EP-OS-0 052 510 describes the impregnating or embedding of luteinizing hormone-releasing hormone in polymeric materials as, for example, poly-lactic acid or poly-lactic acid/polyglycol acid copolymers.

When administered into a patient's body by subcutaneous injection or implantation, the medically impregnated polymer slowly dissolves and releases the medically active substance over several days or even months. The frequency of injection of such compositions can be reduced drastically and consequently patient compliance, as well as the effectiveness of the medicine, can be increased.

The manufacture of such gradually released medical compositions can be achieved by methods disclosed in the literature, including:

Micro-Encapsulation with Organic Solvents (L. M. Sanders et al., J. Contr. Release 2(1985) 187 or P. B. Deasy, Microencapsulation and Related Drug Processes, M. Dekker, Inc., New York, 1984);

Emulsification and Subsequent Vaporization of Solvent Means (T. R. Tice & R. M. Gilley, J. Contr. Release, 2 (1985) 343;

Spray Drying (D. L. Wise et al., Life Science, 19 (1976) 867);

Extrusion (A. J. Schwope et al, Life Science, 17 (1975) 1877);

Fusible Embedding (A. J. Schwope et al, Life Science, 17 (1975) 1877); and

Boundary Surface Polymerization (G. Birrenbach & P. Speiser, J. Pharm. Science, 65 (1976) 1763).

The methods disclosed in the cited literature, however, have either the disadvantage that they require use of large amounts of toxic organic solvents whereby the resulting polymer embedded compositions have high solvent residue concentrations, as see J. P. Benoit et al, Int. J. Pharmaceutics, 29 (1986) 95, or the methods require use of high temperatures or pressures, which lead particularly to high local temperature increases which can damage the embedded medicines, as see L. M. Sanders et al, J. Pharm. Science 75 (1986) 356. If the medical composition remains under the skin or bodily tissue for a long period of time, local toxic tissue reactions can be expected from the organic solvents. For this reason, the amount of solvent residue in the product has to be reduced as completely as possible.

In addition to the solvents in the polymer matrix, one finds that approximately 1 to 2% of the dispersing solvent has been absorbed at the surface of micro particles manufactured by the emulsion method. The solvent cannot be removed by a washing process. As a rule, silicon oil or another lipophilic liquid is used which has the disadvantage of not being degradable by the patient's body, as see EP-OS-81 305 426.9.

Further, all micro-particles (for example, nano capsules) manufactured by polymerization contain mono-, di- and oligomers in the polymer matrix, and often polymerization initiator molecules as well. All of these substances bestow on the micro-particles toxicological characteristics which must be regarded as considerably worse.

Boundary surface polymerization as well as the emulsion procedures have not been successfully transferred from a small scale technical method to a full scale manufacturing operation or production so that commercial introduction of respective products or preparations has not taken place and the so-called nano capsule patent teaching (Speiser DE 296 5725) has not changed this.

Finally, many methods which use organic solvents do not operate in closed systems. Thus, the burden on the environment is considerable. The necessary purification of the air by means of recovery plants is expensive and becomes problematical technically with large throughput as is customary with spray drying.

An essential requirement of the above-described medicine embedded compositions is the sterility of the products. The methods mentioned above do not per se result in sterile products. Either the entire manufacturing process must be carried out under sterile or aseptic conditions with great expense or the product must be sterilized after its manufacture. At present, post-sterilization by means of gamma rays is customary. Apart from governmental regulations which place strict conditions on the marketing of products which have been sterilized with gamma rays this type of sterilization damages the medical ingredient, in particular, if the product contains a peptide medication. The polymer matrix as well, for example the poly-lactic acid, can be decomposed by gamma rays. Thus, release of the medical ingredient from the product or the solubility characteristics of the medical ingredient can change uncontrollably, as see L. T. Sanders et al., J. Contr. Release, 2 (1985) 187.

SUMMARY OF THE INVENTION

It is a purpose of this invention to provide a method for the manufacture of a preparation comprising a substance or substances, desirably a medically useful substance, and a carrier or carriers, desirably a pharmaceutically acceptable carrier, which avoids or lacks a solvent residue, or at least reduces the solvent residue to a toxicologically harmless amount.

Furthermore, it is an object of this invention to provide a method for the manufacture of a product or composition comprising a substance or substances and a polymer or polymers as carrier(s) which are free of mono-, di- and oligomers as well as from polymerization initiator molecules.

Another object of this invention is to provide a method for the manufacture of a product comprising a substance or substances and a carrier or carriers in which sterilization of the product takes place during the process under conditions outside of governmental regulations and which are absolutely safe and harmless as to product quality.

Finally, an object of this invention is to provide apparatus for use in practicing the inventive method.

According to one embodiment of the invention a method is provided for the manufacture of a product or composition comprising a substance or substances and a carrier or carriers, in which a liquid medium containing the substance or substances, and the carrier or the carriers, is brought into contact with a supercritical gas; the supercritical gas is expanded; and the substance/carrier product free of liquid medium is obtained.

The liquid medium used in the method can be one in which the substance(s), as well as the carrier(s), are dissolved or dispersed, or the substance(s) is/are dissolved and the carrier(s) is/are dispersed, or the substance(s) is/are dispersed and the carrier(s) is/are dissolved.

One can mix the substance(s) with a liquid medium on the one hand, and mix the carrier(s) with a liquid medium separately on the other hand and then combine the two mixtures by adding one to the other.

According to another embodiment of the invention a method is provided for the manufacture of a product comprising a substance and a carrier in which a liquid medium containing the substance(s) and the carrier(s) are brought in contact with a supercritical gas wherein the substance(s) and/or carrier(s) is/are soluble; the supercritical gas is expanded; and a liquid medium-free substance/carrier product is obtained.

According to a further embodiment of the invention a method is provided for the manufacture of a product comprising a substance or substances and a carrier or carriers wherein (1) the substance(s) are brought in contact with a supercritical gas in which the substance(s) is/are soluble, and thereupon the supercritical gas is brought in contact with a liquid medium containing the carrier(s), or (2) the carrier(s) is/are brought in contact with a supercritical gas in which the carrier(s) is/are soluble and thereupon the supercritical gas is brought in contact with a liquid medium containing the substance or the substances; the supercritical gas is expanded; and a substance/carrier product free of the liquid medium is obtained.

Examples of carriers suitable for use in this invention are polymer materials. Of course, according to the invention, products can be produced comprising a substance and a carrier plus one or more additives or supplementary components. Thus, in addition to the substance and carrier, the supplementary component, for example, can be a tenside or surface active agent.

Examples of active substances useful in the method are well known medicines, toxins, pesticides, insecticides, herbicides, viruses, and diagnostic materials. We refer to U.S. Pat. No. 3,773,919, the entire content of which is incorporated herein by reference, for a list of medicines useful in the method.

Some of the liquid media useful in the process are formic acid, ethanol, acetic aldehyde, acetone, benzene, bromine, isobutyl alcohol, butyl alcohol, chlorobenzene, chloroform, hydrocyanic acid, diethyl ether, dioxane, acetic acid, heptane, hexane, methyl alcohol, methyl acetate, methylene chloride, octane, pentane, isopentane, isopropyl alcohol, propyl alcohol, pyridine, carbon disulfide, nitrogen tetroxide, carbon tetrachloride, toluene and water although generally all customary inorganic and organic solvents are useful.

Examples of supercritical gases useful in the process are ethane, ethyl chloride, ethylene, ethylene oxide, ammonia, butadiene, butylene, hydrofluoric acid, isobutane, carbon dioxide, methane, methylamine, methyl chloride, propane, propene, nitric oxide, nitrous oxide, dinitrogen dioxide, nitrogen, trimethylamine, vinylbromide, vinylchloride and hydrogen.

The method of extracting lipophilic substances by means of gases at a pressure above the supercritical point has been known to those versed in the food technology art and in chemical technology for a long time, as see G. M. Schneider, Extraction With Supercritical Gases, published: Chemie. Weinheim, 1980. This method is used, for example, in the decaffeination of coffee, extraction of aromatic substances from plants, the de-oiling of lecithin, and for the purification of polymers, as see DE-OS 3 323 940. In order to increase the extract exploitation of plant cells, the cells are first broken open after a pressure treatment with a supercritical gas, by means of a sudden expansion of the gas. This method is called cell cracking.

Surprisingly, it has been found that the resulting product obtained by means of the method according to this invention not only has a prolonged substance release span but it is also totally sterile. However, it was previously known that extracts obtained by means of extraction with supercritical gases are sterile. It must be understood, however, that a sterile product is obtained only when the extract is separated from the extraction residue via the gas phase using procedures such that no microorganisms could enter the extract via the gas phase.

However, it is surprising that according to the method of this invention, a completely sterile extraction residue constituting the substance/carrier product is obtained. This is particularly surprising since according to the present state of the art a reduction in microorganism count and disinfection seem to be possible without sterilization (Compare E. Stahl and G. Rau. Dtsch. Apoth. Journal 125, 1999 (1985); E. Stahl, G. Rau and H. Kaltwasser, Naturwissenschaften 72, 144 (1985). The microorganism reduction is expressly described as uneconomical, since one has to work with high pressure (about 2500 bar) and correspondingly expensive machines.

The germicidal effect of the method of the invention has been proven with many test microorganisms, that is with bacteria as well as fungi and yeasts. Thus, a 30-minute action of a supercritical gas ($CO_2$, 40° C./140 bar) led to the destruction of the following microorganisms:

*Bacillus subtilis spores*
*Bacillus stearothermophilus*
*Escherichia coli*
*Salmonella edinburgh*
*Staphylococcus aureus*
*Pseudomonas aeruginosa*
*Candida albicans*

*Aspergillus niger*

Finally, according to a further embodiment of this invention, apparatus is provided for carrying out the method of the invention. The apparatus comprises a liquid gas pump; a spray tower; a separator for the substance/carrier product; if needed, a separator for the optional medium; and a condenser for the supercritical gas.

Single or multi-nozzles can be used as nozzles, through which the liquid medium can either be atomized through a single opening or through a sintered disk into the spray tower. The single nozzle opening can be 0.2 mm; and in a sintered disk nozzle the opening can be about 10 $\mu$m. If one uses two nozzles, the substance can be dispersed in one liquid medium and the carrier can be dispersed in a separate liquid medium. The two separate dispersions can be atomized separately or together into the spray tower.

DETAILED DESCRIPTION OF THE DRAWINGS

Figure 1:
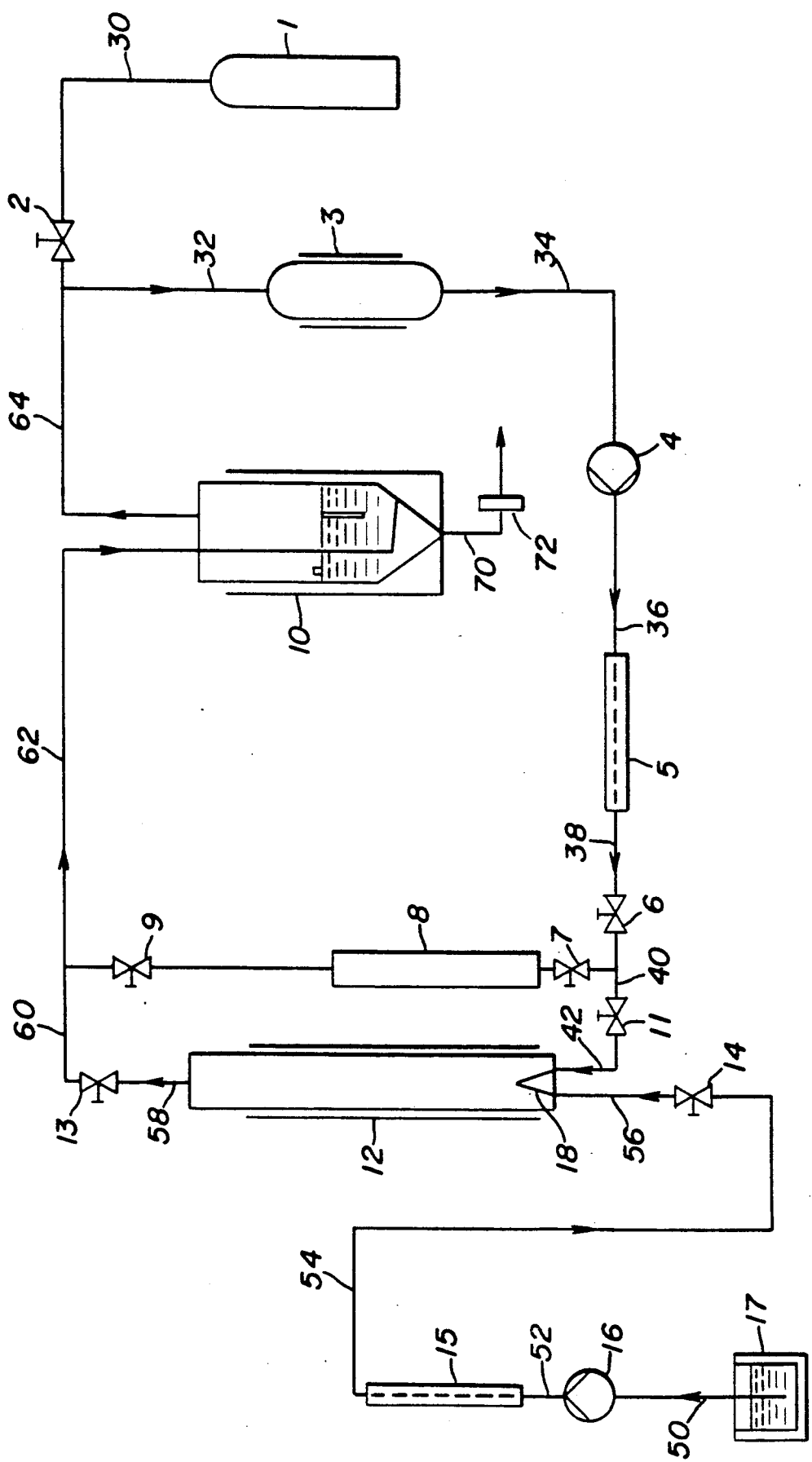
FIG. 1 shows a first embodiment of apparatus for carrying out a method according to the invention.

An apparatus according to this invention is illustrated by FIG. 1 and it can have, for example, a pressure resistant spray tower 12, a liquid gas pump 4, two heat exchangers 5, 15, a separator 10, a product pump 16, and a condenser 3.

The gas or liquefied gas can be taken from pressure gas bottle 1 and fed by conduit 30 through gas inlet valve 2 to conduit 32 which delivers the gas to gas condenser 3 where it is liquefied. The condensed liquefied gas is fed from condenser 3 to conduit 34 which delivers the gas to gas pump 4. The gas is fed from gas pump 4 to conduit 36 which delivers the gas to heat exchanger 5 which supplies heat energy to bring the gas to supercritical conditions. The gas at supercritical conditions is removed from heat exchanger 5 by conduit 38 and fed through distribution valve 6, conduit 40, gas inlet valve 11 and conduit 42 to single or multiple media nozzle 18 in the bottom of spray tower 12. Inlet valve 7 to extractor 8 is closed as is the extractor outlet valve 9.

Liquid medium is withdrawn by conduit 50 from liquid reservoir 17 and is fed by liquid medium pump 16 through conduit 52 to liquid medium heat exchanger 15. The liquid medium contains a dissolved or dispersed suitable carrier and an effective or active substance. The liquid medium exits heat exchanger 15 into conduit 54 which feeds it to liquid medium inlet valve 14. The liquid medium flows from valve 14 to conduit 56 which delivers the liquid medium to nozzle 18. The liquid medium containing the carrier and the active substance are atomized through nozzle 18 with the supercritical gas, fed by conduit 42, into the spray tower 12.

The gaseous mixture is removed from spray tower 12 by conduit 58 and fed through outlet valve 13 to conduits 60, 62 which deliver the mixture to separator 10.

The liquid medium is separated in separator 10 from the super-critical gas which is removed through conduit 64 and is fed to condenser 3 and then reintroduced into the closed loop by gas pump 4. The liquid medium can be removed from separator 10 with the product. By using a closed loop the liquid medium and supercritical gas are not lost and thus cannot contaminate the environment.

In the described direct concurrent parallel flow method the supercritical gas extracts the liquid medium from the solution or dispersion so that the carrier is obtained as a solid containing the active substance embedded therein. The solid carrier containing the embedded active substance can be removed from the bottom of separator 10 by conduit 70 and fed through filter 72 thereby giving the product in sterilized form.

Figure 2:
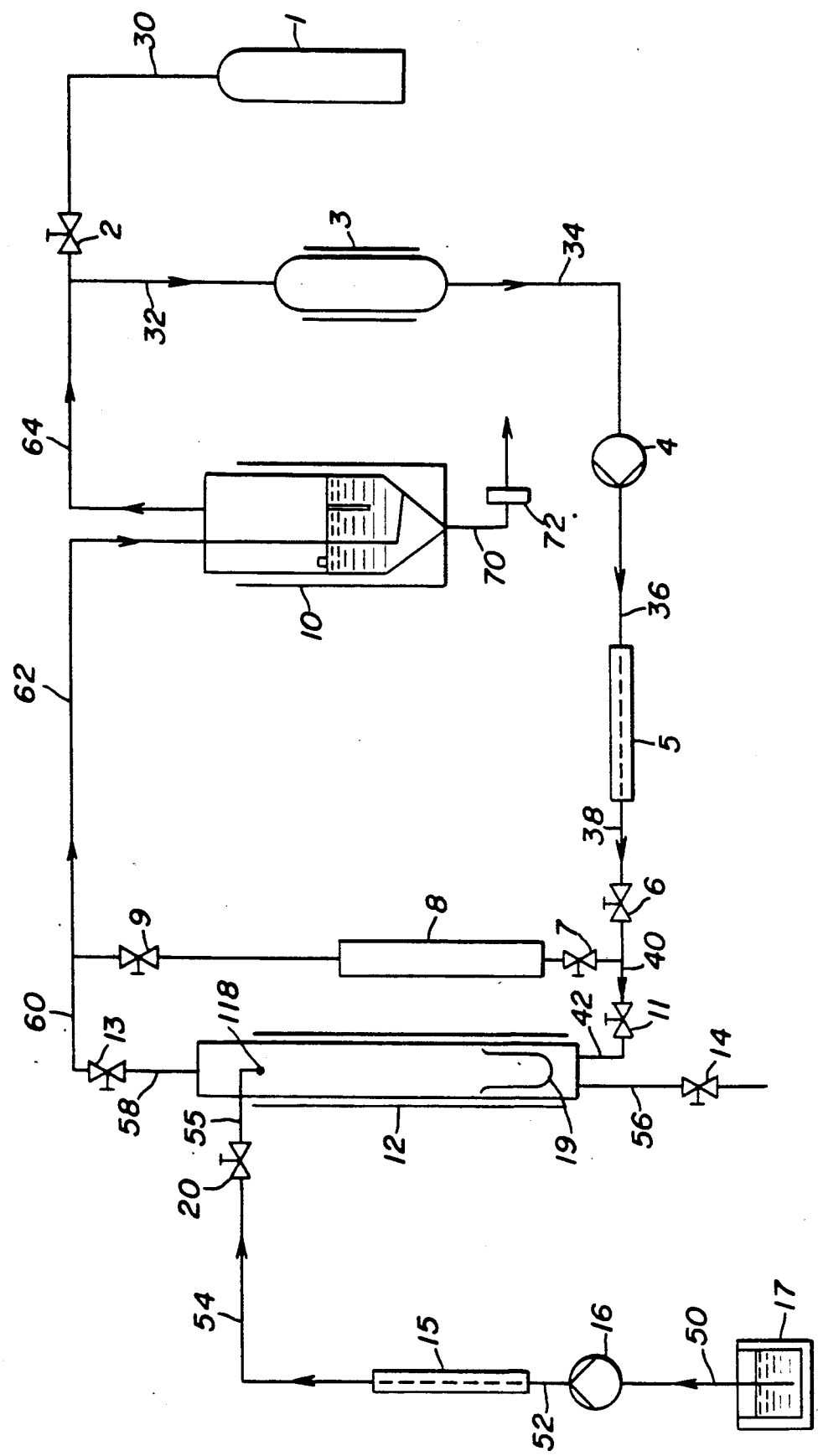
FIG. 2 shows a second embodiment of apparatus for carrying out a method according to the invention.

FIG. 2 illustrates a second embodiment of apparatus provided by the invention. This embodiment, however, is similar to the embodiment illustrated by FIG. 1 so only the differences will be described. As shown in FIG. 2, the liquid medium containing the carrier and active substance is fed by conduit 54 through spray tower inlet valve 20 to single or multi-port nozzle 118 located in the upper part of the spray tower 12. The dispersion or solution of liquid medium, carrier and active substance is atomized downwardly in the spray tower 12 in a counter flow direction to the supercritical gas fed into the bottom of the spray tower by conduit 42. The supercritical gas removes the liquid carrier in the spray tower and leaves the desired product comprising the carrier having the active substance embedded therein. The product collects at the bottom of the tower in receiver 19 from which it is withdrawn in sterile form. In this embodiment valves 7 and 9 are closed.

Figure 3:
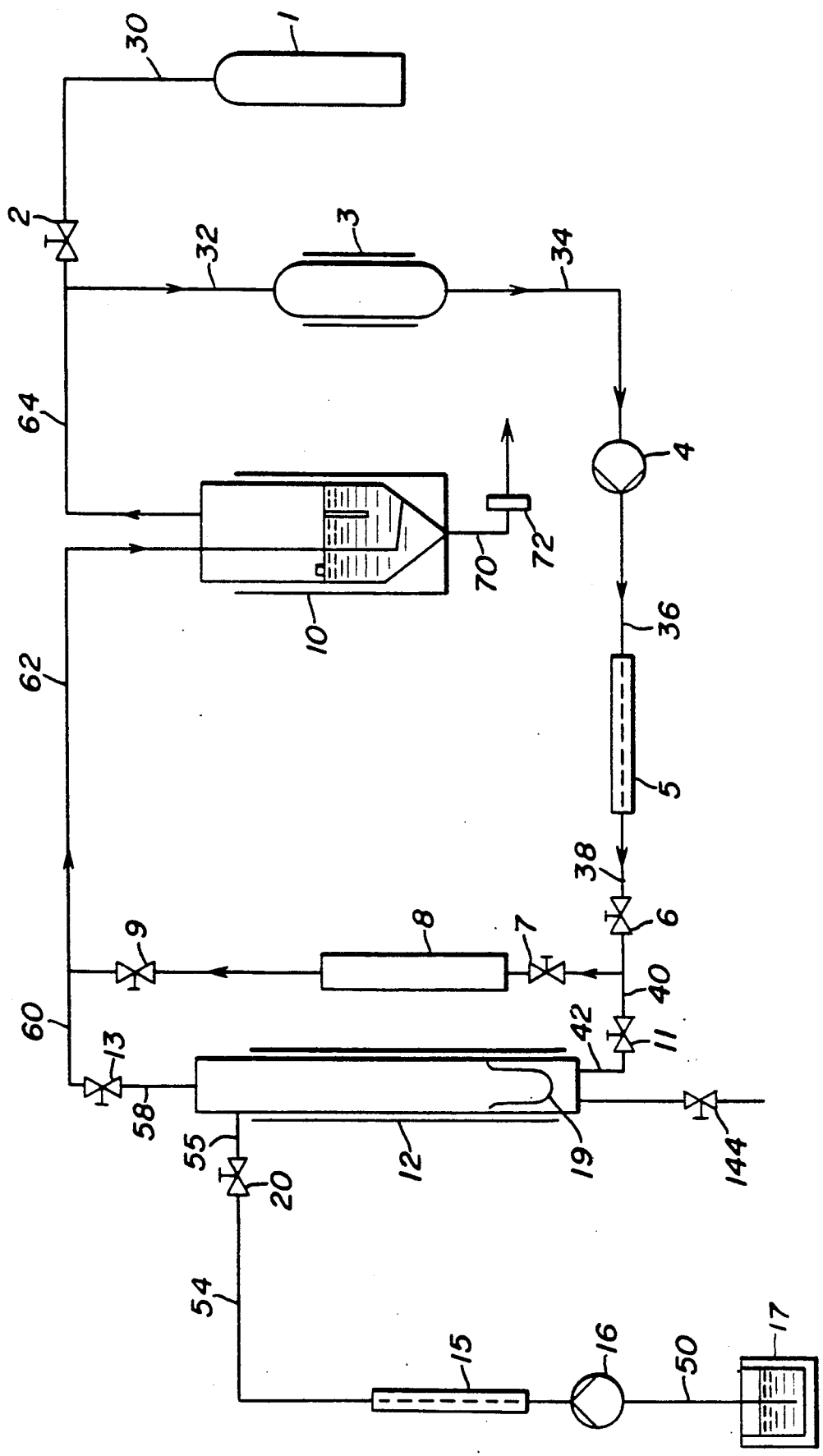
FIG. 3 shows a third embodiment of apparatus for carrying out a method according to the invention.

Another embodiment of the invention is illustrated by FIG. 3. Since FIG. 3 is similar to FIG. 1 only the differences in FIG. 3 will be described. Valves 11 and 13 are shut. Valve 144 is an exhaust valve. The supercritical gas containing a carrier and an active substance is fed into the system by conduit 30 and after going through condenser 3, pump 4, heat exchanger 5 and distribution valve 6 it is fed through extractor inlet valve 7 to extractor 8 where the gas is extracted from the carrier and active substance. The product consisting of the active substance embedded in the carrier is separated from the gas in separator 10.

Figure 4:
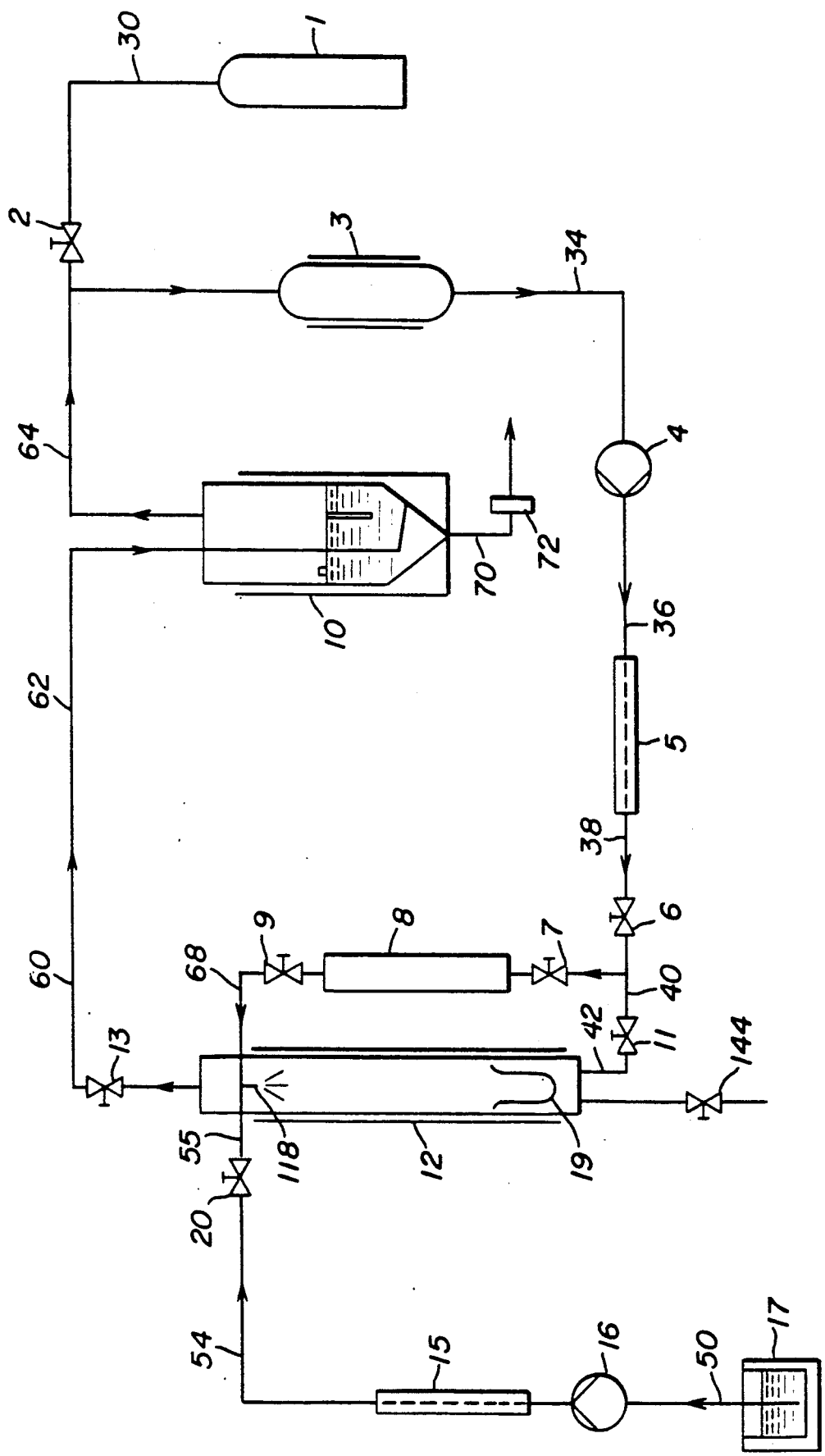
FIG. 4 shows a fourth embodiment of apparatus for carrying out a method according to the invention.

Still another embodiment of the invention is illustrated by FIG. 4 which is similar to FIG. 1 so only the differences will be described in detail. In this embodiment valves 7, 9, 11 and 13 are open. In FIG. 4, valve 144 is a pressure exhaust valve. A liquid medium can be fed through valve 20 and conduit 55 into the top of spray tower 12 and atomized through nozzle 118. The liquid medium can contain a carrier or an active substance. A supercritical gas can be fed through valve 7 into extractor 8 containing a carrier or an active substance. Here the supercritical gas dissolves the active substance and/or the carrier and then it flows through valve 9 to conduit 68 for delivery to nozzle 118 from which it is atomized simultaneously with the liquid medium fed by conduit 55. At the same time, supercritical gas is fed by conduit 42 into the bottom of spray tower 12. The feed stream of supercritical gas comes in contact with the atomized solution or dispersion of a carrier or solvent and removes the dispersion medium atomized through nozzle 118.

Supercritical gases, at certain pressure/temperature combinations, possess a capacity or ability to dissolve polymers, lipids, lecithins or waxes used as carriers, as see F. P. Schmitz, J. Chromatography 356 (1986) (261). Accordingly, the above described apparatus can include in the direction of flow ahead of the separator 10 a pressure resistant extractor and the supercritical gas can be charged with the carrier(s) and the substance(s), and separated as an embedded substance/carrier product from the separator 10 via a nozzle.

Of course, one can charge the supercritical gas with the substance(s) only, or only with the carrier(s), and supply the carrier(s) or respectively the substance(s), with the aid of the component or ingredient pump 18, to the separator 10. In this case one obtains a carrier shell containing the substance or an adsorbate comprising the substance absorbed on the carrier.

The invention is explained further in detail by two examples.

EXAMPLE 1

One gram of d,1(+)-poly-lactide is mixed with specified amounts of the following microorganisms:

| Microorganism | Concentration: Microorganism/g |
| --- | --- |
| Bacillus subtilis (spores) | $10^2$, $10^3$ m $10^4$ |
| Bacillus stearothermophilus (spores) | $10^2$, $10^3$, $10^4$ |
| E. coli | $10^4$ |
| Salmonella edinburgh | $10^4$ |
| Staphylococcus aureus | $10^4$ |
| Pseudonomas aeruginosa | $10^4$ |
| Candida albicans | $10^4$ |
| Aspergillus niger | $10^4$ |

Samples of the contaminated polymers are treated statically with $CO_2$ at 140 bar and 50° C., and 140 bar and 40° C., for 12 hours or 0.5 hour respectively. Subsequently, gas expansion takes place for about 1 minute. The samples are then subjected to sterility tests.

Result: All samples are sterile.

Parallel investigated samples, which had not been treated with $CO_2$, revealed that d,1(+)-poly-lactide, MW 17.000 (PLA 17.000) does not itself have microorganism sterilizing capability.

EXAMPLE 2

Embedding by Spraying

Figure 5:
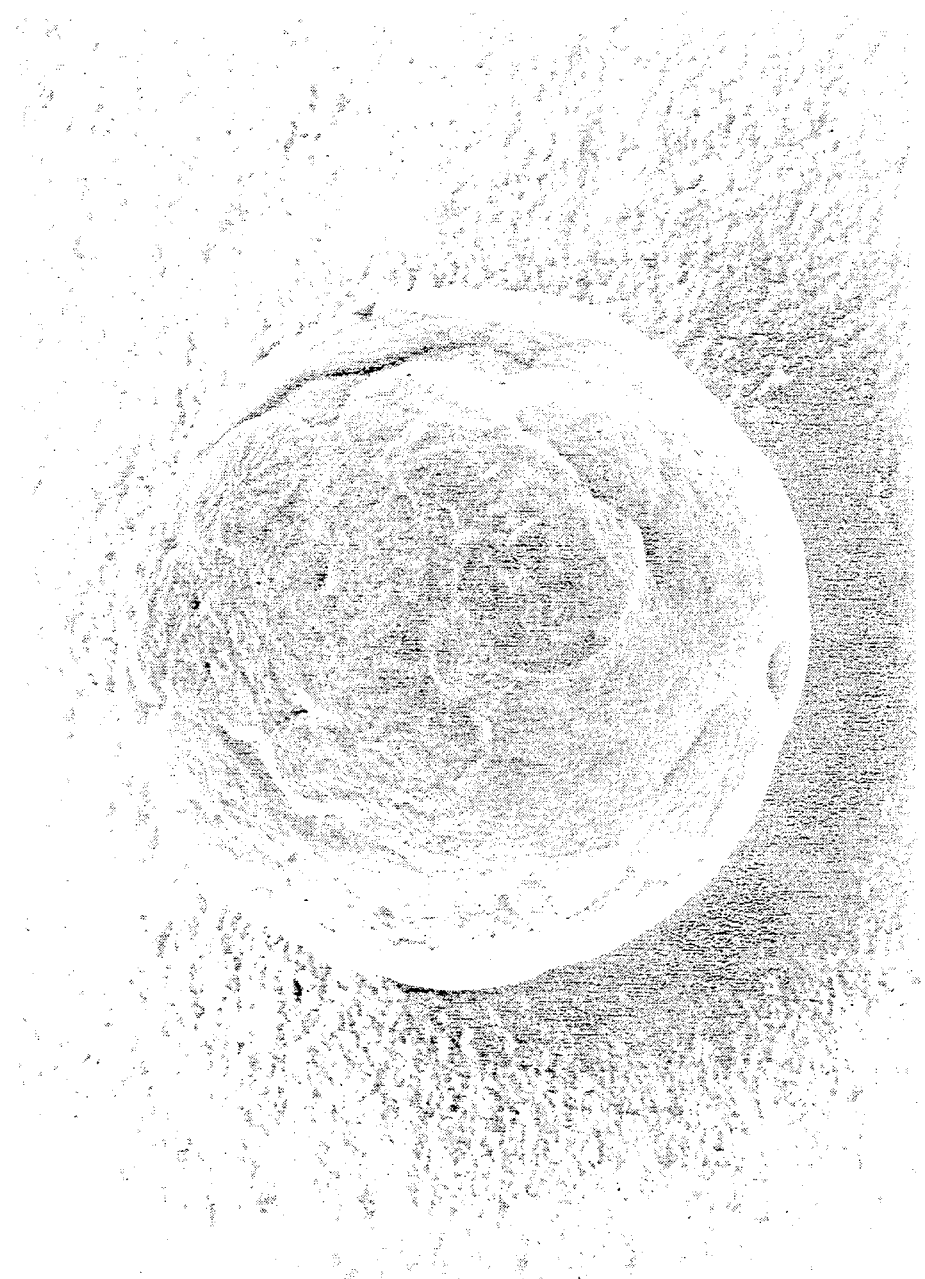
FIG. 5 shows the substance/carrier product of Example 2 produced using the apparatus illustrated by FIG. 3.

A 0.02 percent clonidin-HCl solution in $CH_2CL_2$, which contains 20% of PLA 17,000 is atomized in the extraction column of the high-pressure plant at 100 bar excess pressure. At the same time, $CO_2$ is supplied to the column in counterflow at 100 bar and 60° C. Atomization takes place through a nozzle of sintered metal (pore size about 5 to 10 $\mu$m). After falling a distance of a few centimeters a dry powder is obtained which consists of spheres (about 100 $\mu$m) (FIG. 5). The spheres are composed of sub-units which presumably represent the primary droplets up to 10 $\mu$m in size. The primary droplets presumably form the larger spheres shortly after leaving the nozzle.

EMBEDDED SUBSTANCE RELEASE

The release of the embedded clonidin-HCl was followed over a 24 hour period at 37° C. in a phosphate buffer (pH=7.5).

| Time in hours | Clonidin - HCl released (%) |
| --- | --- |
| 1.5 | 40.5 |
| 5 | 48.8 |
| 24 | 52.0 |

Method: High Pressure Liquid Chromatography

As in all published articles on the release of a substance from PLA microspheres, the substance which is superficially absorbed or embedded respectively in the upper layers of the polymers is quickly released in the initial phase while the remainder of the dose migrates out of the polymer over a period of several days and is released into the body.

An acceleration of the release rate can be achieved by increasing the substance concentration, reduction of the polymer molecular weight, the use of surface characteristics, through the use of hydrophilic carrier substances, or the use of hydrophilic auxiliary substances.

What is claimed is:

1. A method for the manufacture of a product comprising at least one substance embedded in a carrier comprising:
   feeding into a nozzle and contacting a liquid medium containing at least one substance and at least one carrier with a supercritical gas thereby forming a gaseous mixture of the supercritical gas and the liquid medium containing at least one substance and at least one carrier; and
   separating the gaseous mixture of supercritical gas and liquid medium from the substance and the carrier thereby producing a sterilized product comprising at least one substance embedded in the at least one carrier.

2. A method according to claim 1 in which a liquid medium is used in which both the substance and the carrier are dissolved in the liquid-medium.

3. A method according to claim 1 in which a liquid medium is used in which the substance is dissolved and in which the carrier is dispersed.

4. A method according to claim 1 in which a liquid medium is used in which the substance is dispersed and in which the carrier is dissolved.

5. A method according to claim 1 in which a liquid medium is used in which the substance and the carrier are dispersed in the liquid medium.

6. A method for the manufacture of a product comprising at least one substance embedded in a carrier comprising:
   contacting a substance with a supercritical gas in which the substance is soluble;
   contacting the supercritical gas containing the dissolved substance with an atomized liquid medium containing a carrier to form a gaseous mixture of the supercritical gas containing the substance and the atomized liquid medium containing the carrier;
   expanding the gaseous mixture to separate supercritical gas and liquid medium from the substance and the carrier thereby producing a sterilized liquid medium-free product comprising the substance embedded in the carrier; and
   withdrawing the separated gaseous mixture of supercritical gas and liquid medium from said product, separating the liquid medium from the supercritical gas, condensing the supercritical gas to a liquid, and, by means of a liquid gas pump, recycling the liquefied supercritical gas in a closed loop into contact with further quantities of the substance.

7. A method for the manufacture of a product comprising at least one substance embedded in a carrier comprising:
   contacting a substance with a supercritical gas in which the substance is soluble;
   contacting the supercritical gas containing the dissolved substance with a carrier
   thereby forming a gaseous mixture of the supercritical gas containing the substance and carrier; and
   by expanding the gaseous mixture separating the supercritical gas from the substance and the carrier thereby producing a sterilized product comprising the substance embedded in the carrier.

8. A method according to claim 7 in which the gaseous mixture is expanded into contact with a liquid medium; and
   a product comprising the substance embedded in the carrier is obtained free of supercritical gas and liquid medium.

9. A method for the manufacture of a product comprising at least one substance embedded in a carrier comprising:
   contacting a carrier with a supercritical gas in which the carrier is soluble;
   contacting and mixing the supercritical gas containing the dissolved carrier with an atomized liquid medium containing a substance to form a gaseous mixture of the supercritical gas containing the carrier and the atomized liquid medium containing the substance; and
   separating the supercritical gas and liquid medium from the substance and the carrier thereby producing a sterilized liquid medium-free product comprising the substance embedded in the carrier.

10. A method according to claim 1, 6 or 9 in which the supercritical gas is a member of the group consisting of nitrous oxide, carbon dioxide, a halogenated hydrocarbon, a saturated hydrocarbon, an unsaturated hydrocarbon, nitrogen, dinitrogen dioxide and ammonia.

11. A method according to claim 1, 6 or 9 in which the carrier is selected from the group consisting of polymers, lipids, lecithins, waxes and mixtures thereof.

12. A method according to claim 1, 6 or 9 in which the substance is a member of the group consisting of a medicine, toxin, virus, diagnostic material, herbicide, insecticide and pesticide.

13. A method for the manufacture of a product comprising at least one substance embedded in a carrier comprising:
   feeding a supercritical gas to a supercritical gas condenser to condense the gas;
   feeding the condensed supercritical gas from the supercritical gas condenser to a liquid gas pump;
   feeding the supercritical gas from the liquid gas pump through conduit means to a supercritical gas heat exchanger;
   feeding the supercritical gas from the supercritical gas heat exchanger through conduit means to and through a nozzle in a spray tower;
   feeding a liquid medium containing a substance and a carrier to and through a conduit to the nozzle;
   removing a mixture of supercritical gas and liquid medium dissolved in supercritical gas from the spray tower by conduit means and feeding said mixture to a separator;
   removing supercritical gas from the separator by conduit means and feeding it to the gas condenser; and
   removing liquid medium from the separator, and recovering a sterilized dry powder comprising spheres of the carrier having the substance embedded therein from the spray tower.

14. A method for the manufacture of a product comprising at least one substance embedded in a carrier comprising:
   feeding supercritical gas by conduit means through a heat exchanger to an extractor containing a substance;
   removing a mixture of the supercritical gas and the substance from the extractor by conduit means and feeding the mixture to the nozzle in a spray tower;
   feeding a solution of a carrier dissolved in a liquid medium into the nozzle in the spray tower;
   removing a mixture of supercritical gas and liquid medium from the spray tower by conduit means and feeding said mixture to a separator;
   removing supercritical gas from the separator by conduit means and feeding it to a gas condenser;
   removing liquid medium from the separator; and
   withdrawing a substance embedded in the carrier in sterile form from the spray tower.

15. A method for the manufacture of a product comprising at least one substance embedded in a carrier comprising:
   atomizing a liquid solution of at least one substance and at least one carrier dissolved in an organic solvent into a column while also feeding a supercritical gas into the column in counterflow to the flow of the atomized liquid solution so that the atomized liquid solution and the supercritical gas are brought into intimate contact with each other to thereby form a mixture;
   removing the mixture of supercritical gas and organic solvent from the column and feeding it to a separator in which the organic solvent and the supercritical gas are separated from the mixture by expansion leaving a product in the column in the form of a dry powder comprising spheres of the carrier having the substance embedded therein; and
   withdrawing the product from the column.

16. A method for the manufacture of a product comprising at least one substance embedded in a carrier comprising:
   atomizing a liquid solution of at least one substance and at least one carrier dissolved in an organic solvent into a column while also feeding a supercritical gas into the column so that the atomized liquid solution and the supercritical gas are brought into intimate contact with each other to thereby form a mixture; and
   removing the mixture from the column and separating the organic solvent and the supercritical gas from the mixture thereby leaving a product in the form of a dry powder comprising spheres of the carrier having the substance embedded therein.

17. A method for the manufacture of a product according to claim 15 or 16 wherein the product withdrawn from the column is sterile.

18. Apparatus for producing a product comprising at least one substance embedded in a carrier comprising:
   a supercritical gas condenser;
   conduit means to feed condensed supercritical gas from the gas condenser to a liquid gas pump;
   conduit means to feed condensed supercritical gas from the liquid gas pump to a supercritical gas heat exchanger;

conduit means to feed supercritical gas from the heat exchanger to a nozzle in a spray tower;

conduit means to feed a liquid medium containing a member of the group consisting of a substance and a carrier to the nozzle in the spray tower;

conduit means for removing supercritical gas, liquid medium and a member of the group consisting of a substance and a carrier from the spray tower and feeding it to a separator;

conduit means for removing supercritical gas from the separator and feeding it to the gas condenser; and means for removing liquid medium from the separator.

19. Apparatus according to claim 18 including:

an extractor;

conduit means for feeding supercritical gas containing a substance from the heat exchanger to the extractor; and conduit means for removing supercritical gas and the substance from the extractor and feeding them to the separator.

* * * * *